(12) United States Patent
Jhaveri et al.

(10) Patent No.: US 7,030,236 B2
(45) Date of Patent: Apr. 18, 2006

(54) ANTISENSE OLIGONUCLEOTIDES TARAGETING FOLATE RECEPTOR ALPHA, AND THE USE THEREOF

(76) Inventors: Mona Savitri Jhaveri, 10101 Grosvenor Pl., Apt. #402, Rockville, MD (US) 20852; Patrick Clay Elwood, 4931 Yantis Dr., Albany, OH (US) 43054; Koong-Nah Chung, 8011 Davis Dr., St. Louis, MO (US) 63105

(*) Notice: Subject to any disclaimer, the term of this patent is extended or adjusted under 35 U.S.C. 154(b) by 381 days.

(21) Appl. No.: 10/093,523

(22) Filed: Mar. 11, 2002

(65) Prior Publication Data

US 2003/0050267 A1   Mar. 13, 2003

Related U.S. Application Data

(60) Provisional application No. 60/274,249, filed on Mar. 9, 2001.

(51) Int. Cl.
| | |
|---|---|
| *C07H 21/04* | (2006.01) |
| *C07H 21/02* | (2006.01) |
| *A61K 48/00* | (2006.01) |
| *C12N 12/00* | (2006.01) |

(52) U.S. Cl. .................. 536/24.5; 536/24.1; 536/23.1; 514/44; 435/320.1

(58) Field of Classification Search ............... 536/23.1, 536/24.1, 24.5; 514/44; 435/6, 320.1
See application file for complete search history.

(56) References Cited

U.S. PATENT DOCUMENTS

| | | | | |
|---|---|---|---|---|
| 5,998,148 A * | 12/1999 | Bennett et al. | ................. | 435/6 |
| 6,096,880 A * | 8/2000 | Kool | ......................... | 536/25.3 |
| 6,180,353 B1 * | 1/2001 | Dean et al. | .................... | 435/6 |

OTHER PUBLICATIONS

Hansen et al., Teratology vol. 59(6):385, Jun. 1999.*
Jhaveri et al., Proceedings of the American Association for Cancer Research Annual Meeting, No. 41, p. 643, Mar. 2000.*
Xin-Lau et al The Journal of Biological Chemistry, vol. 271(41):25539-25547, 1996.*

* cited by examiner

*Primary Examiner*—Sean McGarry
(74) *Attorney, Agent, or Firm*—Fleshner & Kim, LLP

(57) ABSTRACT

The invention relates to treatment of cancers and cancerous cells which over-express α folate receptor (FRα) compared to the normal cells of the same tissue. The invention is directed to antisense oligonucleotides which are complimentary to the coding region of FRα, as well as the pharmaceutical compositions made thereof, and the methods of using the same for treatment of cancers, e.g. cancers of ovary, cervix, uterus, and brain.

11 Claims, 11 Drawing Sheets

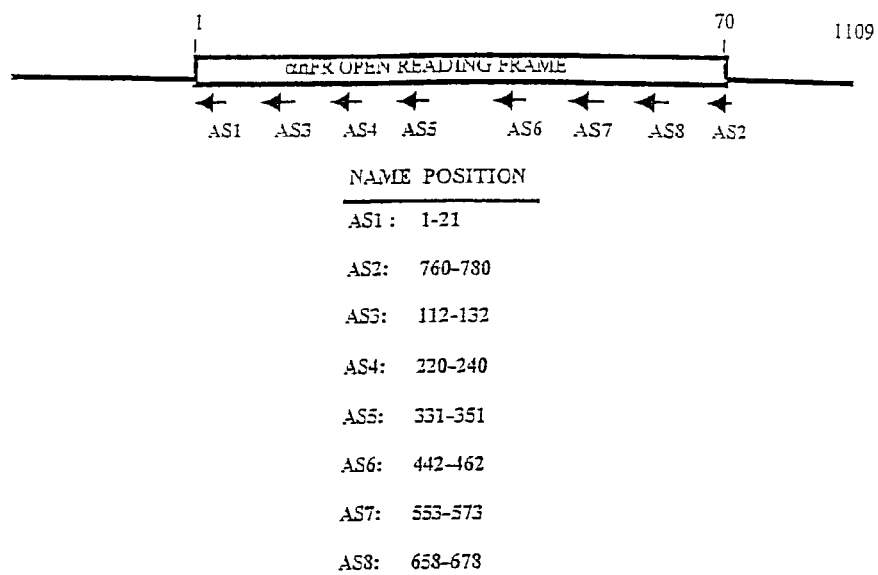
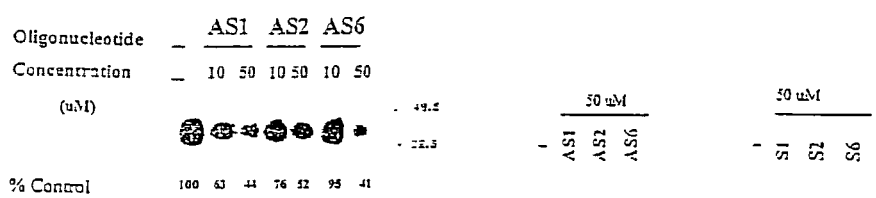
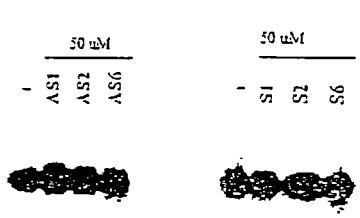
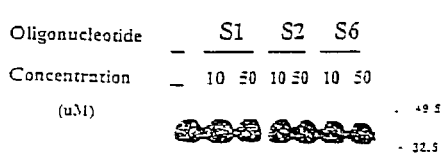
Figure 2

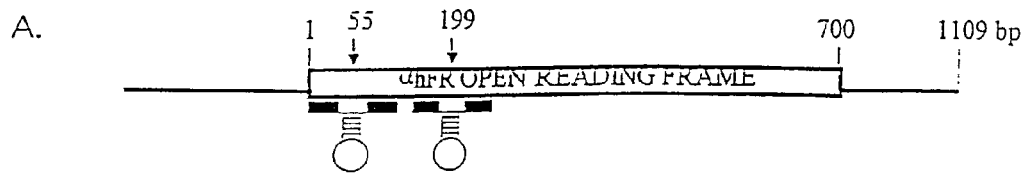
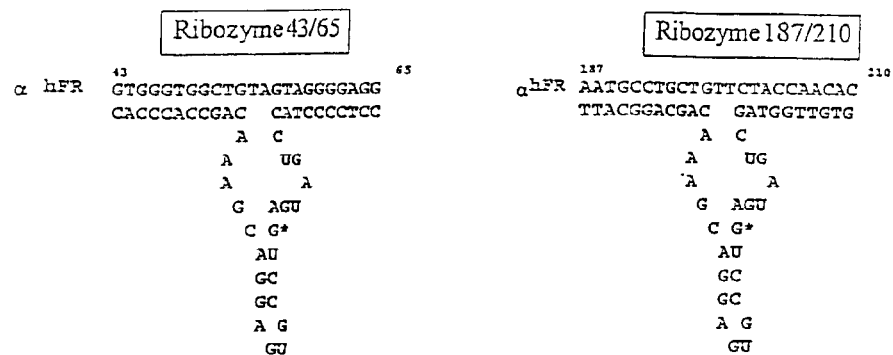
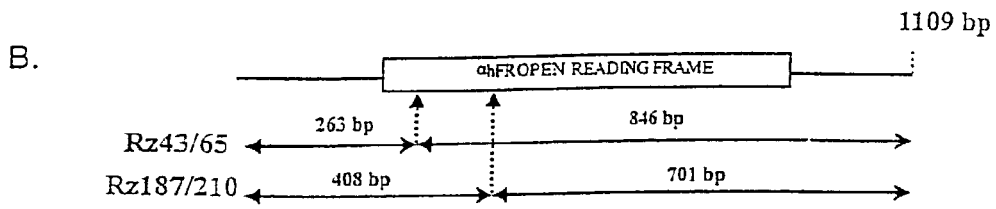
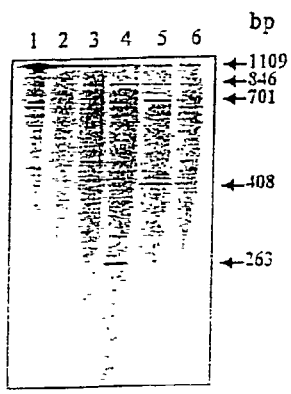
Figure 4

Figure 5
A.
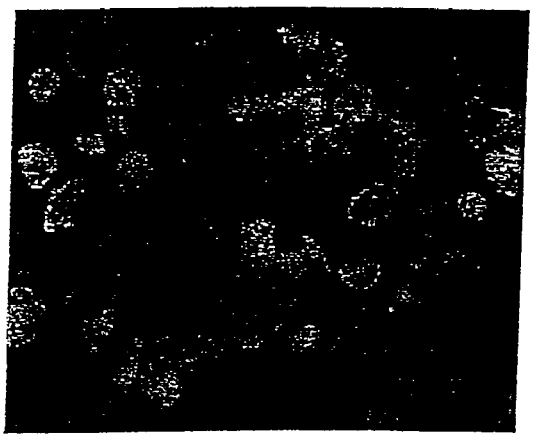
B.
C.
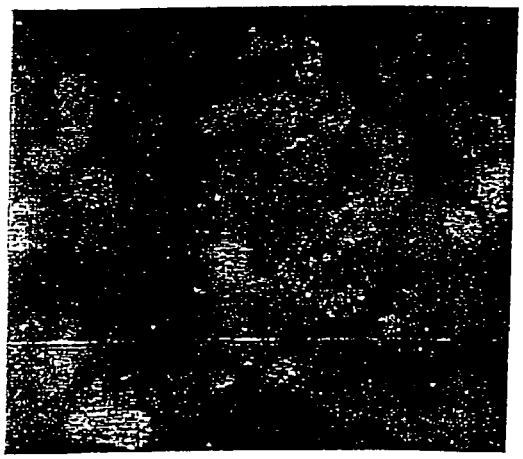

A.
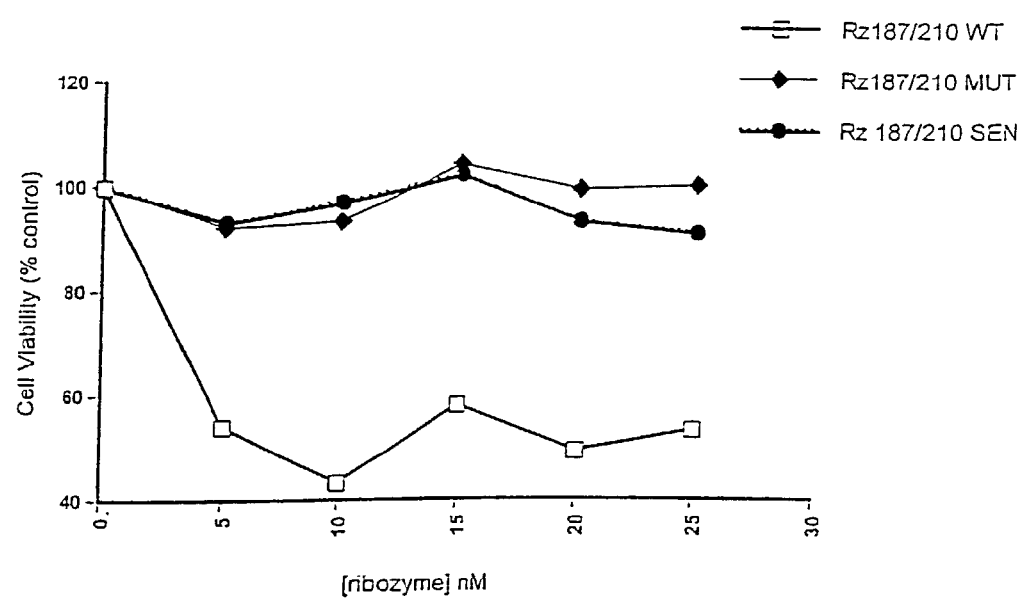
B.
Figure 6

Figure 9

FIGURE 10
A.
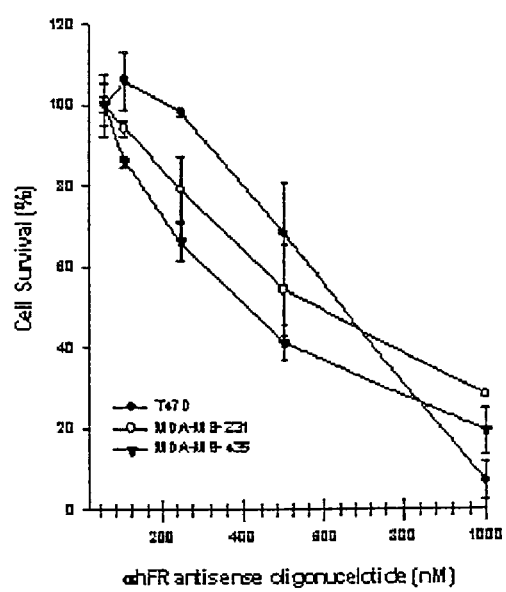
B.
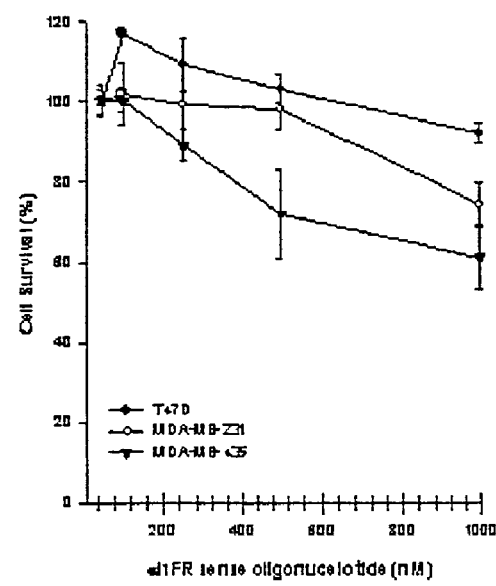

ANTISENSE OLIGONUCLEOTIDES TARAGETING FOLATE RECEPTOR ALPHA, AND THE USE THEREOF

CLAIM TO PRIORITY

This non-provisional application claims priority to U.S. Provisional Application No. 60/274,249, filed on Mar. 9, 2001, the entire disclosure of which is incorporated herein by reference.

STATEMENT AS TO RIGHTS TO INVENTIONS MADE UNDER FEDERALLY-SPONSORED RESEARCH AND DEVELOPMENT

The present invention was made with government support. Accordingly, the United States government has certain rights in the invention.

BACKGROUND OF THE INVENTION

1. Field of the Invention

The invention is in the field of medicinal chemistry. In particular, the invention relates to certain antisense oligonucleotides and the use thereof for the treatment of cancer.

2. Background of the Related Art

Folate vitamins are essential components of intracellular metabolic pathways that transfer single carbon groups during nucleic acid and amino acid synthesis. In particular, folate is essential for de novo synthesis of deoxythymidylate triphosphate (dTTP), which incorporates into cellular DNA during DNA replication and repair.

Folate exists in three forms differing by oxidation state. Folic acid is the most oxidized form, whereas dihydrofolate and tetrahydrofolate are progressively more reduced. The tetrahydrofolate form recieves single carbon atom groups and transfers them in various biosynthetic pathways. During transfer, tetrahydrofolate is oxidized to dihydrofolate. Dihydrofolate is in turn reduced by the enzyme dihydrofolate reductase (DHFR), completing a metabolic cycle and preparing tetrahydrofolate to again receive single carbon atom groups.

Folate inhibition impairs cell growth, and thus folate-dependent metabolic pathways have long been exploited as chemotherapeutic targets. For example, the folate analog methotrexate (MT) is a successful antifolate chemotherapy agent due to its potent inhibition of DHFR. Newer antifolates are now in clinical trials.

Folates and antifolates enter cells via two major transport systems. The predominant carrier in normal tissue has a high affinity for reduced folates, and relatively low affinity for folic acid. These biochemical characteristics account for its name, reduced folate carrier (RFC). The second transport system includes transmembrane folate receptor (FR) isoforms, referred to as FR-α, FR-β, and FR-γ. These receptors have high affinity for folic acid and intermediate affinity for reduced folate forms.

In most normal cells, there is little or no expression of FR isoforms, and their physiologic role, if any, remains to be determined. Interestingly, however, FR isoforms are known to be expressed in various malignant tissues. In particular, FRα is highly expressed in many carcinomas of epithelial cell origin, such as ovarian carcinoma. It is possible that FR expression is related in some way to the abnormal growth characteristics of such cells.

Antifolates such as MTX are transported avidly by the RFC, but not by FR isoforms. In cancer cells, reduced RFC expression may promote chemotherapy resistance by reducing the cell's ability to take up antifolates. In such cancer cells, the FR isoforms may serve as an alternative folate transport mechanism, thereby promoting cancer cell growth.

In early 1990s, Matsue et al., (Proc. Natl. Acad. Sci. U.S.A. 89: 6006-6009, 1992) and Luhrs et al. (J. Clin. Invest. 90: 840–847, 1992) observed that expression of FRa enabled cultured mouse keratinocyte and fibroblasts cells to grow in low folate media. Matsue et al. suggested that cells vary in their folate requirement, with rapidly proliferating cells such as malignant cells requiring high levels of folate to survive. They further intimated that the growth potential of malignant cells may be directly related to the level of folate receptor expression.

About the same time, in 1991, Westerhof et al. (Cancer Research 51: 5507–5513, 1991) reported on experimental results that concluded that FRa expression enhanced antifolate uptake in L1210 cells. In addition, they showed that FRa mediated uptake of thymidylate synthase inhibitors, a related class of anticancer agents. Importantly, their data demonstrated that FRα expression markedly inhibited the growth of L1210 cells when the cells were exposed to antifolates or thymidylate synthase inhibitors. Hence, began a line of research focusing on the increased expression of FRα in malignant cells and its use for specific targeting and delivery of anti-cancer drugs to malignant cells.

In 1993, Chung et al. (J. Clin. Invest. 91: 1289–1294, 1993) published the results of their investigation on FRα-mediated transport in a methotrexate resistant human breast cancer cell line (MCF-7 cells). The investigators stably transfected MCF-7 cells with human FRα cDNA, and evaluated cell growth, and folate and antifolate transport. Although, there was a positive correlation between cell growth and FRα expression when cells were grown in low folate media, they observed that FRα expression also enhanced MTX uptake and cellular sensitivity to the negative growth effects of MTX. Hence, in line with the findings of Westerhof et al., it was suggested that the increased expression of FRα would be desirable as it provided a means for cancer therapy using the chemotherapeutic drug, MTX.

Subsequently, Sun et al. (J. Clin. Invest. 96: 1535–1547, 1995) transduced human cervical carcinoma (HeLa) cells with recombinant adeno-associated viruses (AAV) expressing FRα in either sense or antisense direction. As expected, the antisense construct suppressed FRα expression, whereas the sense construct increased FRα expression. When cells were grown in supraphysiological levels of folate, suppression of FRα expression with antisense had little effect on cellular proliferation, similar to the control (untransduced cells), and FRα sense expression reduced cellular proliferation. Similar results were obtained in vivo: when transduced cells were transferred to nude mice, cells transduced with antisense FRα grew larger tumors than untransduced cells or sense FRα-transduced cells. The investigators concluded that "there was an inverse relationship between FR expression and cell proliferation in the cells" (emphasis added).

In the same year, Spinella et al. (J. Biol. Chem. 270: 7842–7849, 1995) reported having stably transfected L1210 human leukemia cells with a cDNA expressing FRα. L1210 cells express a nonfunctional reduced folate carrier, and are MTX-resistant. It was observed that FRα-transfected cells were capable of taking up MTX, thereby tending to restore antifolate sensitivity to the cells. Hence, their results seemed to confirm that the high expression of FRα would be desired as it seemed to enhance sensitivity to chemotherapeutic agents.

Gorlick et al., in their 1996 publication (New England Journal of Medicine 335: 1041–1048, 1996), reviewed the problem of methotrexate resistance in acute leukemias. These authors concluded that and related receptors had little or no role in leukemia therapy or antifolate resistance. Instead, they suggested targeting other points in the folate metabolic pathway, such as the dihydrofolate reductase gene.

In 1999, also consistent with the developing line of investigation, Sun et al. (Cancer Research 59: 940–946, 1999) published their results for their research on signal transduction in FRα-transduced HeLa cells, using a protocol essentially identical to that described in Sun et al., 1995. They observed that FRα expression directly correlated with increased thymidine kinase activity in sense and antisense FRα-transduced HeLa cells. Increased thymidine kinase activity induced by FRα increased sensitivity of HeLa cells to azathymidine (AZT), another anticancer chemotherapeutic agent. Antisense suppression of FRα expression reduced thymidine kinase activity and reduced sensitivity to AZT, yet, another indication that antisense supression of FRα was not desirable as it renderd the anti-cancer drug, AZT, ineffective against the disease.

The above references are incorporated by reference herein where appropriate for appropriate teachings of additional or alternative details, features and/or technical background.

SUMMARY OF THE INVENTION

The invention is related to the discovery that inhibiting the expression of FRα, using antisense oligonucleotides, in cancer model systems results in suppression of growth of the cancerous cells. Accordingly, the invention is directed to FRα antisense oligonucleotides and pharmaceutical compositions thereof for the treatment of cancers, e.g. ovarian cancer, wherein the cancerous cells, compared to normal cells of the same tissue, over-express FRα.

In particular, the invention relates to antisense oligonucleotides complementary to a region of the open reading frame of αhFR as shown in FIG. 9. The antisense oligos may be used in pharmaceutical compositions containing a pharmaceutically acceptable carrier, and may be administered alone (as naked DNA) or with a pharmaceutical carrier to patients with cancerous tumors that exhibit high expression of FRα as compared to normal cells of the same tissue. Such cancers include but are not limited to the cancers of ovary, cervix, uterus, and brain.

The antisense oligonucleotide of the invention may be of a wide variety of sizes but preferably about 10–50 nucleotides long, and most preferably about 18 to 21 nucleotides long. The most preferred antisense oligos of the present invention are AS1 (Sequence ID. No 2), AS2 (Sequence ID No. 3), and AS6 (Sequence ID. No. 4).

The present invention also relates to the structural derivatives of the disclosed antisense oligos, such as but not limited to antisense oligos wherein the internucleotide linkages are phosphodiesters or phosphorothioate phosphodiesters.

The antisense oligos of the present invention may be administered as two antisense oligonucleotides which are complementary to adjacent regions in the open reading frame of αhFR as shown in FIG. 9.

The antisense oligos of the present invention may be contained within a wide variety of vectors and/or delivery vehicles, such as but not limited to plasmids and ribozyme. The ribozyme containing the antisense oligo may be of any variety, such as but not limited to a hammerhead ribozymes.

Such ribozymes may be monomeric or multimeric. The ribozymes of the present invention, particularly the multimeric ones, may be co-administered with magnesium supplements.

BRIEF DESCRIPTION OF THE DRAWINGS

The invention will be described in detail with reference to the following drawings:

FIGS. 2A–2D: 2A depicts various antisense 21-mer oligonucleotides targeted to the αhFR open reading frame. 2B–2D depict that KB cells incubated with 50 µM of AS-1, AS-2, or AS-6 (FIG. 2B) reduced the levels of newly synthesized αhFR by up to approximately 60% compared to KB cells treated with the sense oligonucleotide controls (FIG. 2C). In contrast, Northern analysis of αhFR mRNA remained unaffected by AS1, AS-2 or AS-6 treatment (FIG. 2D).

FIG. 3 depicts a bar graph indicating decreased viability of cells treated with αhFR antisense oligonucleotides.

FIGS. 4A–4B: 4A schematically depicts two ribozymes targeted to the 5' region of the αhFR open reading frame. 4B demonstrates efficient cleavage of in vitro synthesized αhFR mRNA sequences by in vitro synthesized αhFR-targeted ribozymes.

FIGS. 5A–5C: 5A is a color photograph of KB cells wherein the nuclei are DAPI stained (blue). 5B is a color photograph of KB cells wherein the oligonucleotides are FITC-labeled (green). 5C is a color photograph of KB cells showing that the DAPI stained nuclei (blue) and FITC-labeled oligonucleotides (green) colocalize well.

FIGS. 6A–6B: 6A depicts a graph showing that Rz 187/210 WT significantly decreased cell survival by approximately 60% compared to the control mutant and sense ribozymes, Rz 187/210 MUT and Rz 187/210 SEN. 6B shows the rapid rate of ribozyme decay.

FIG. 9: FIG. 9 depicts the sequence of human-binding protein cDNA(SEQ ID No. 1). The complete cDNA nucleotide sequence (upper line) and deduced amino acid sequence (lower line) are shown. The numbering is for the nucleotide bases and starts at the initiation ATG codon. A polyadenylation signal (AATAAA) at position 879 is underlined. The amino acids are represented by their single letter designation and the termination codon (TGA) at position 872 is indicated by a -.

FIGS. 10A–10B: FIGS. 10A and 10B depict the effect of various concentrations of αhFR AS-6 oligonucleotide (A) and S-6 oligonucleotide (B) on survival of cultured human breast cancer cells. End-modified phosphorothioated oligonucleotides were transfected into $2 \times 10^4$ cells at the indicated concentrations for 6 hrs using a Tf-liposome-mediated delivery complex. Cell survival was assessed 48 hrs after transfection by XTT assay.

FIG. 11 depicts chemosensitization of MDA-MB-435 breast cancer cells after combination treatment with αhFR AS6 oligonucleotide and doxorubicin. MDA-MB-435 cells were plated at $2\times10^4$ cells/well and transfected with 500 nM of αhFR AS6 or S6 end-modified phosphorothioated oligonucleotide. After 24 hrs, cells were incubated with media containing doxorubicin at the indicated concentrations. Cell survival was determined by XTT assay after 72 hrs.

DETAILED DESCRIPTION OF PREFERRED EMBODIMENTS

Figure 1:
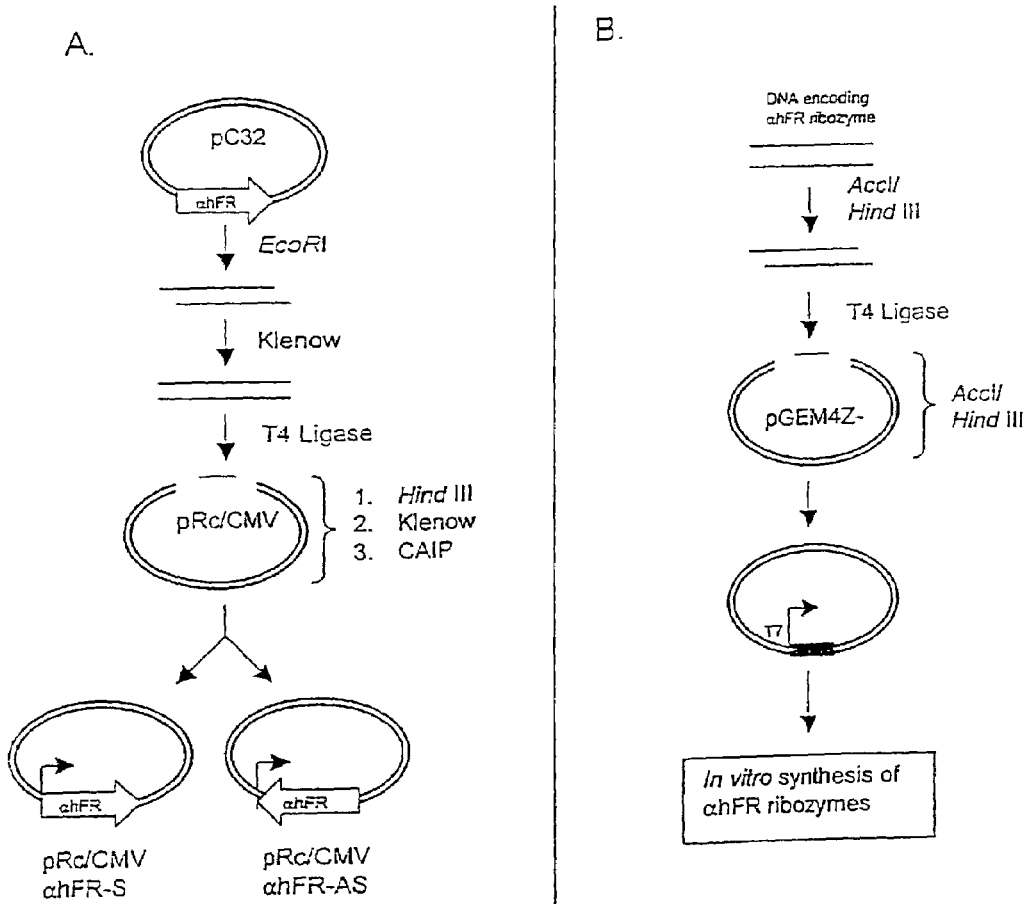
FIGS. 1A–1B: 1A depicts the construction of the plasmids carrying the sense- and antisense-oriented αhFR cDNAs subcloned into the eukaryotic expression vector pRc/CMV. 1B depicts the construction of the ribozyme constructs that contain DNA oligonucleotides encoding αhFR wild type ribozymes (rz43/65 WT and rz 187/210 WT) and mutant (rz43/65 MUT and rz 187/210 MUT) or sense (rz43/65 S and rz 187/210 S) ribozymes which were directionally inserted into pGEM4Z.

Folates are cofactors and are essential for cell survival. They are known to participate in various biochemical processes, including DNA and RNA synthesis and reactions involving transmethylation. The human α folate receptor (αhFR) is involved in mediating intracellular folate uptake and may also play a role in cellular proliferation. Additionally, αhFR is increased in some malignancies (i.e. cancer of the ovaries, cervix, uterus, and brain). See Cancer Wu M. et al., *Expression of folate receptor type alpha in relation to cell type, malignancy, and differentiation in ovary, uterus, and cervix* Epidemiol Biomarkers Prev 8(9):775–82 (1999). The present invention provides a method for therapy of cancerous tumors that express αhFR such as ovarian cancer.

The present invention results from the investigations characterizing FRα expression and growth in cancer cell lines. The inventors suspected and, therefore, investigated a possible link between FRα expression and abnormal growth. Expression vectors were constructed encoding human FRα in the sense and antisense direction and used to stably transfect various cancer cell lines. While stably transfected colonies were readily obtained in FRα-transfected cells, such colonies were never observed in FRα antisense-transfected cells. This result showed that FRα antisense has a significant negative impact on cell growth.

To further investigate the effect of FRα expression on cell growth, the inventors used antisense oligonucleotides to diminish FRα expression. Antisense therapy is the administration of exogenous oligonucleotides which bind to a target polynucleotide located within the cells. The term "antisense" refers to the fact that such oligonucleotides are complementary to their intracellular targets, e.g., FRα mRNA. The FRα antisense oligonucleotides of the present invention include structural derivatives such as S-oligonucleotides (phosphorothioate derivatives or S-oligos, see for example, Jack Cohen, OLIGODEOXYNUCLEOTIDES, Antisense Inhibitors of gene expression, CRC Press, 1989; and Synthesis 1:1–5 (1988), and U.S. Pat. No. 6,172,217) which exhibit enhanced cancer cell growth inhibitory action.

Hence, antisense oligonucleotides and corresponding sense controls were designed based on the human FRα open reading frame. The oligonucleotides were introduced into KB cells, a human nasopharyngeal carcinoma cell line with high FRα expression. Three of the antisense oligonucleotides significantly reduced FRα expression and markedly inhibited KB cell growth, whereas the sense oligonucleotide controls had no effect on FRα expression or cell growth In addition to antisense oligonucleotides, FRα expression was also targeted with hammerhead ribozymes that specifically cleaved nucleotide sequences in the human FRα mRNA. To enhance cellular uptake, the ribozymes were introduced into cells in a polylysine-folic acid complex, which increases FR-mediated endocytosis of the ribozymes. Using this approach, substantial ribozyme uptake was documented in HeLa and KB cells after six hours of exposure to the ribozyme-polylysine-folic acid complex. Moreover, the FRα-targeted ribozymes were shown, in vitro, to cleave radiolabeled FRα mRNA, whereas control ribozymes had no activity towards FRα mRNA.

Further, confirmatory animal studies are designed, using an animal model system, wherein the size and rate of growth of the subcutaneous tumors are monitored subsequent to the administration of anti-sense oligos of αhFR. Any slowing, cessation, or reversal of the tumor growth indicates effectiveness of the anti-sense oligos in vivo. Decreased αhFR protein levels in excised tumors also indicates specificity of αhFR antisense oligos for target sequence in vivo.

Preferably, however, the antisense oligonucleotides of the present invention inhibit expression of the folate receptor by at least about 10%, but more preferably by about 10–15, 15–20, 25, 33, 30–45, 50, 60, 55–70, 75, 80–90, or 100 percent.

S-oligos (nucleoside phosphorothioates) are isoelectric analogs of an oligonucleotide (O-oligo) in which a non-bridging oxygen atom of the phosphate group is replaced by a sulfur atom. The S-oligos of the present invention may be prepared by treatment of the corresponding O-oligos with 3H-1,2-benzodithiol-3-one-1,1-dioxide which is a sulfur transfer reagent. See Iyer, R. P. et al, J. Org. Chem. 55:4693–4698 (1990); and Iyer, R. P. et al., J. Am. Chem. Soc. 112:1253–1254 (1990), the disclosures are which are fully incorporated herein by reference.

Figure 9:
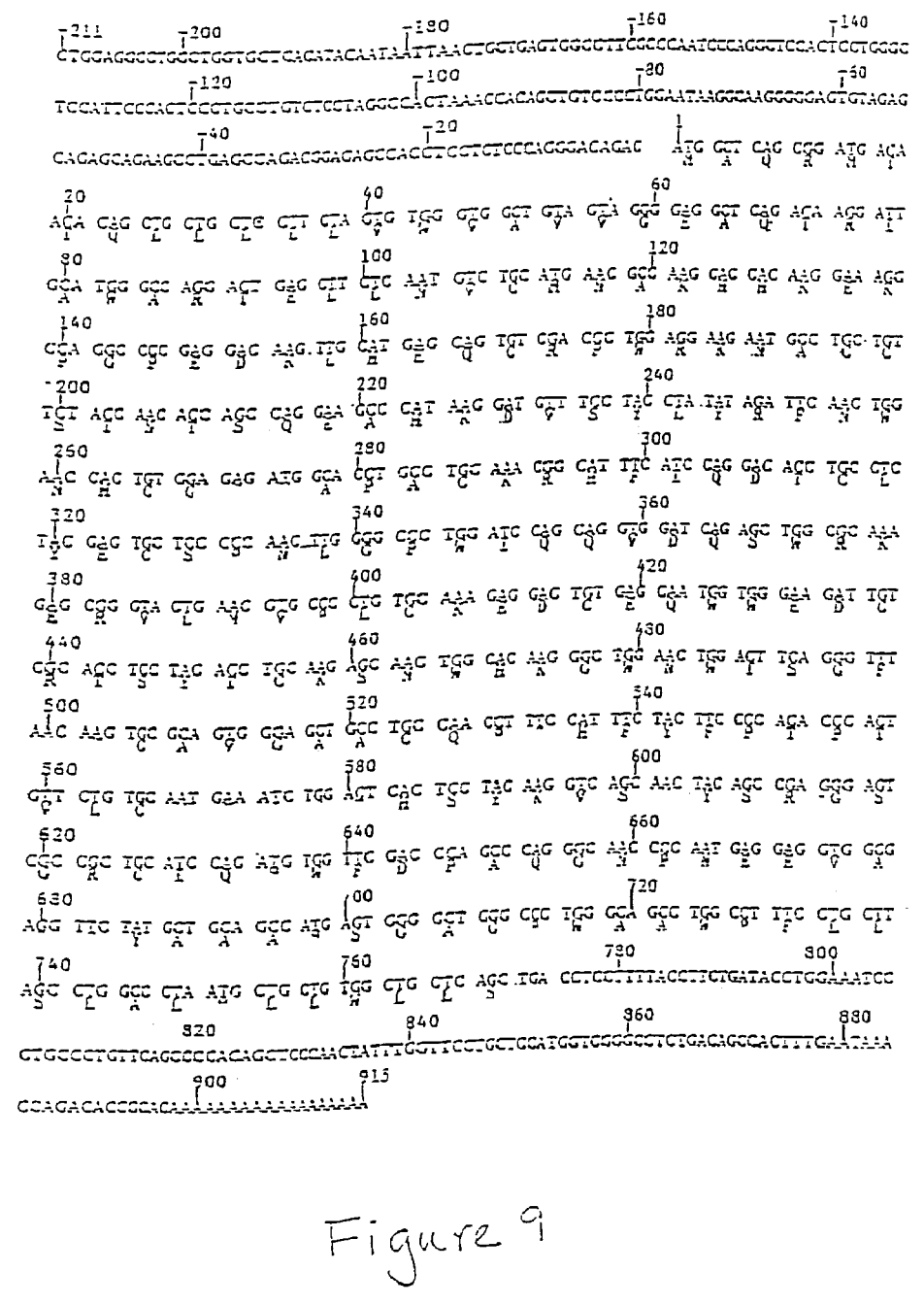

The FRα oligonucleotides of the present invention may be DNA or RNA of a size less than the full coding sequence of the FRα. The full sequence of FRα is shown in FIG. 9, wherein the open reading frame (OFR) is shown in upper case letters. The lower case letters indicate the untranslated region. Under the OFR sequences is the corresponding amino acid sequences of the FRα protein.

Preferably, the size of the oligos is less than that of the open reading frame, i.e. 774 bases. The oligos may be from about 10 to 773 nucleic acids long, the preferred embodiments may be 12-100, 12-80, 12-50, 12-35, 12-30, 12–21, 18-21, 15-100, 15-80, 15-50, 15-35, 15-30 nucleic acids long, and the most preferred embodiment is 21 nucleic acids long. In deciding the lower size limit of the oligos, it is important to choose a size that would render the hybridization with the target, FRα, specific, i.e. about 12 nucleic acids long.

However, depending upon how the oligos are used, the sequences may be broken up into smaller fragments. For example, in the Examples of the present invention, sometimes the antisense oligos were used as pairs, one inserted in each arm of the ribozyme. When the oligos are used as part of a ribozyme, specific design considerations have to be followed. Ribozymes are RNA sequences that have catalytic activity, which is used to knock out target gene's function. The two arms of the ribozyme of the present invention, which flank the ribozyme's catalytic core structure, contain the antisense RNA sequences. One arm (Helix I) requires at least about 6 base pairs of the antisense sequence and the other arm (helix III) requires at least about 9 base pairs of antisense RNA sequence. To increase target specificity, the ribozyme arms may be made longer by using longer antisense sequences, as described above. However, as the length of the arms increases, the catalytic activity of the ribozyme may decrease. Hence, a balance is struck between target specificity and catalytic effectiveness.

Hence, when pairs of antisense oligonucleotides are incorporated into a ribozyme for cellular transfection, the size of the oligo in Helix I may be as low as about 6 nucleotides long. The size of the oligo in Helix III, however, may be as low as about 9–10 nucleotides long.

The main factor in deciding the size of a given oligonucleotide is whether or not it will be specific for hybridizing to, hence inhibiting, the target sequence. The upper limit for the size of the oligo should be decided, taking into account the specific sequences within the oligonucleotide which might form secondary structures. Secondary structures are not desirable as they reduce and/or inhibit the ability of the antisense oligo to hybridize with the target.

It is preferred to use an oligo that is rather small, most preferably around 18–22 nucleic acids long. As mentioned above, larger oligos may form secondary structures and fail to hybridize the target well if at all. The oligos are designed empirically, and are screened for efficacy by for example, introducing them into KB cells alongside proper controls to determine if and to what degree a given oligo reduces translation of the FRα protein from mRNA, and/or if and to what degree the oligo inhibits cell proliferation.

When selecting a sequence target for the antisense oligonucleotides, the following additional guidelines should also be taken into account: (a) choose sequences within the open reading frame (not the untranslated regions); (b) consider targeting the initial translated sequences (the first AUG site) to prevent formation of functional truncated proteins; (c) the target sequence should have low secondary structure (see below for various ways of determining the RNA secondary structure), and (d) target sequences should not contain repetitive/redundant sequences.

The RNA secondary structure may be determined using a variety of methods. For example by using RNA folding programs (e.g. but not limited to MFOLD by Genetics Computer Group, Madison, Wis., USA). Alternatively, RNAseH which cleaves RNA/DNA complexes can be used to determine which areas of the mRNA are not folded and hence available for targeting by antisense oligos. Briefly, target mRNA molecules are allowed to hybridize with complementary DNA, and the complex is incubated with RNAseH. RNAseH will cut only in those regions of the mRNA devoid of secondary structure, and therefore available for targeting by antisense oligos. Yet another method of determining the RNA secondary structure is to form a ribozyme library. The full antisense sequence of the OFR is shut guned into the ribozyme arms; the antisense ribozymes are then allowed to act on the target mRNA; and assayed (forexample using rapid amplification of cDNA ends (RACE)) to select the ones that are effective against the target mRNA.

Preferred target sequences within the coding region of αhFR are those of AS1, AS2, and AS6, as well as the sequences surrounding that region. The sequences of AS1, AS2, and AS6 being nucleic acids 1–21, 760–780, and 442–462, respectively, of the OFR, it is preferred to make oligos of various sizes directed to these regions. The preferable regions are, therefore, from about −10 to +100, +680 to +800, and +352 to +552; more preferably, about +1 to +50, +745 to +795, and +435 to +475; and most preferably, about +1 to +35, +752 to +788, and +436 to 468 of the coding region.

The oligos of the present invention may be used singly or in combination, optimizing the inhibition of cell proliferation. For example, a portion of coding region may be targeted by two or more oligos that are complementary to adjacent set of target sequences. In this way, smaller size oligonucleotides may be used avoiding the possible secondary structure formation that could be brought about using longer sequence oligos.

Included in the present invention are pharmaceutical compositions comprising an effective amount of at least one of FRα antisense oligonucleotides of the invention in combination with a pharmaceutically acceptable carrier. In one embodiment, only one type of antisense oligonucleotide is used. In another embodiment, two or more types of antisense oligonucleotides are used. The two or more antisense oligonucleotides may be complementary to an adjacent or non-adjacent region of the FRα coding region. Administration of more than one type of antisense FRα oligonucleotide which are complementary to adjacent regions of the coding region of FRα or the corresponding mRNA may allow for more efficient inhibition of FRα expression and cell proliferation The antisense oligonucleotides of the present invention may be administered alone, as naked polynucleotides. Preferably, the FRα antisense oligonucleotide is coadministered with an agent which enhances the uptake of the antisense molecule by the cells. For example, it may be combined with a lipophillic cationic compound which may be in the form of liposomes. The use of liposomes to introduce nucleotides into cells is known in the art. The following references, for example, describe the method in detail: U.S. Pat. Nos. 4,897,355 and 4,394,448, the disclosures of which are incorporated herein by reference in their entirety. See also U.S. Pat. Nos. 4,235,871, 4,231,877, 4,224,179, 4,753,788, 4,673,567, 4,247,411, 4,814,270 for general methods of preparing liposomes comprising biological materials.

A preferred cationic lipid delivery system for transfecting cells with antisense oligonucleotides is the commercially available Lipofectin. Lipofectin can efficiently deliver polyanionic oligodeoxynucleotides and plasmid DNA into the cytoplasm and nucleus of cells. See Behr, J. P. (1994) Bioconjugate Chem. 5, 382–389. Lipofectin is a 1:1 (wt/wt) liposome formulation of the cationic lipid N-[1-(2,3,-dioleyloxy)propyl]-N,N,N-trimethylammonium chloride (DOTMA) and dioleoylphosphatidylethanolamine (DOPE).

Yet, a more preferred delivery system is the serum-resistant cytofectin, termed GS 2888 cytofectin. See Lewis, J. G. et al., *PNAS USA* 93:3176–3181 (1996). GS 2888 cytofectin efficiently transfects oligodeoxynucleotides and plasmid DNA into many cell types in the presense or absense of 10% serum, uses a 4- to 10-fold lower concentration of the agent as compared to Lipofectin, and is about 20-fold more effective at eliciting antisense effects in the presence of serum when compared to Lipofectin.

In addition, the antisense oligonucleotides of the present invention may be conjugated to a peptide that is ingested by cells. Examples of useful peptides include peptide hormones, antigens or antibodies, and peptide toxins. By choosing a peptide that is selectively taken up by the target cells, specific delivery of the antisense agent may be effected. The antisense oligos of the present invention may be covalently bound via the 5'OH group by formation of an activated aminoalkyl derivative. The peptide of choice may then be covalently attached to the activated antisense oligonucleotidevia an amino and sulfhydryl reactive hereto bifunctional reagent. The latter is bound to a cysteine residue present in the peptide. Upon exposure of cells to the antisense oligonucleotide bound to the peptide, the peptidyl antisense agent is endocytosed and the antisense oligonucleotide binds to the target mRNA to inhibit translation. See PCT Application Publication No. PCT/US89/02363.

A preferred delivery system for the present invention is the receptor mediated intake of the antisense oligos, e.g. folic acid-folate receptor mechanism. In a preferred embodiment, the antisense oligonucleotides of the present invention were introduced into the target cells via folate receptor-mediated transfection, wherein the antisense oligonucleotides (with or without a ribozyme) were bound to a folate-polylysine conjugate which binds a folate receptor and is thereby transferred into the cells.

Various other delivery systems include polymeric compositions containing endosomolytic agents such as the ones described in U.S. Pat. No. 6,077,663, and polymeric compositions that take advantage of cell-type specific receptor-mediated endocytosis to transfer a desired nucleic acid into a given cell's cytoplasm (see for example U.S. Pat. No. 5,922,859).

Many delivery systems have been designed and tested in vivo. Adenoviral vectors, e.g. adeno-associated virus (AAV), currently used in gene therapy human trials. Biodegradable polymer formulations are available that protect DNA from degradation. Dentrimers, similar to polymers, are another preferred delivery system containing multiple functional groups. Also, there are mechanisms for delivey of the antisense oligos with or without the ribozymes across the blood brain barrier for diseases of the central nervous system (CNS). For a review of the various useful delivery systems see Advanced Drug Delivery Reviews, Vol. 44 (2000) pp.

It is intended that in addition to the antisense oligos specifically tested, structural derivatives of the oligonucleotides be used as well. A variety of derivatives of the antisense oligonucleotides are known and have been studied; many are available commercially. The derivatives may be used to enhance efficacy of target inhibition and/or reduce side effects. Basically, the common modifications are made to the linkages, the sugar component, and the base. Common linkage modifications include phosphodiester, methyl phosphonate, phosphorothioate, and phosphoroamidate. The sugar modifications comprise 2'-O-methyl group, 2'-O-methyloxyethoxy. The base modifications comprise 5-propynl pyrimidine. For specific examples of such derivatives see: mixed-backbone oligonucleotides (Hybridon, Inc., U.S. Pat. No. 5,886,165), oligonucleotides containing primary phosphoroamidate internucleoside linkages (Hybridon, Inc., U.S. Pat. No. 6,140,482), triplex-forming antisense oligonucleotides having abasic linkers targeting nucleic acids with mixed sequences of purines and pyrimidines (Hybridon, Inc., U.S. Pat. No. 5,693,773), oligonucleotides having modified CpG dinucleosides (Hybridon, Inc., U.S. Pat. No. 5,856,462), inverted chimeric oligonucleotides (Hybridon, Inc., U.S. Pat. No. 5,973,136), antisense oligonucleotide alkylphosphonothioates and arylphosphonothioates (Hybridon, Inc., U.S. Pat. No. 5,929,226), aminooxy-modified oligonucleotides (Isis Pharmaceuticals, Inc., U.S. Pat. No. 6,194,598, U.S. Pat. No. 6,172,209), oligonucleotides incorporating 2-aminoadenosine (Isis Pharmaceuticals, Inc., U.S. Pat. No. 6,175,004), oligomers having pyrimidine nucleotide (S) with 2' and 5 substitutions (Isis Pharmaceuticals, Inc., U.S. Pat. No. 6,166,197), carbamate-derivatized nucleosides and oligonucleosides (Isis Pharmaceuticals, Inc., U.S. Pat. No. 6,166,188), oligonucleotides with phosphodiester, phosphorothioate, and phosphorodithioate covalent linkages (Isis Pharmaceuticals, Inc., U.S. Pat. No. 6,160,152), oligomers containing diastereomerically enriched phosphorothioate and boranophosphate linkages (Isis Pharmaceuticals, Inc., U.S. Pat. No. 6,160,109), other derivatized oligonucleotides having improved uptake and other properties (Isis Pharmaceuticals, Inc., U.S. Pat. No. 6,153,737), 2'-O-acetamido modified oligomers (Isis Pharmaceuticals, Inc., U.S. Pat. No. 6,147,200), gapped 2' modified oligonucleotides (Isis Pharmaceuticals, Inc., U.S. Pat. No. 6,146,829), 2'-O-alkyl purine phosphoramidites (Isis Pharmaceuticals, Inc., U.S. Pat. No. 6,133,438), 2'-O-aminooxy-modified oligonucleotides (Isis Pharmaceuticals, Inc., U.S. Pat. No. 6,127,533), Phosphotriester oligonucleotides, amidities (Isis Pharmaceuticals, Inc., U.S. Pat. No. 6,124,445), and many more known in the art, or made available commercially from a variety of companies.

Figure 7:
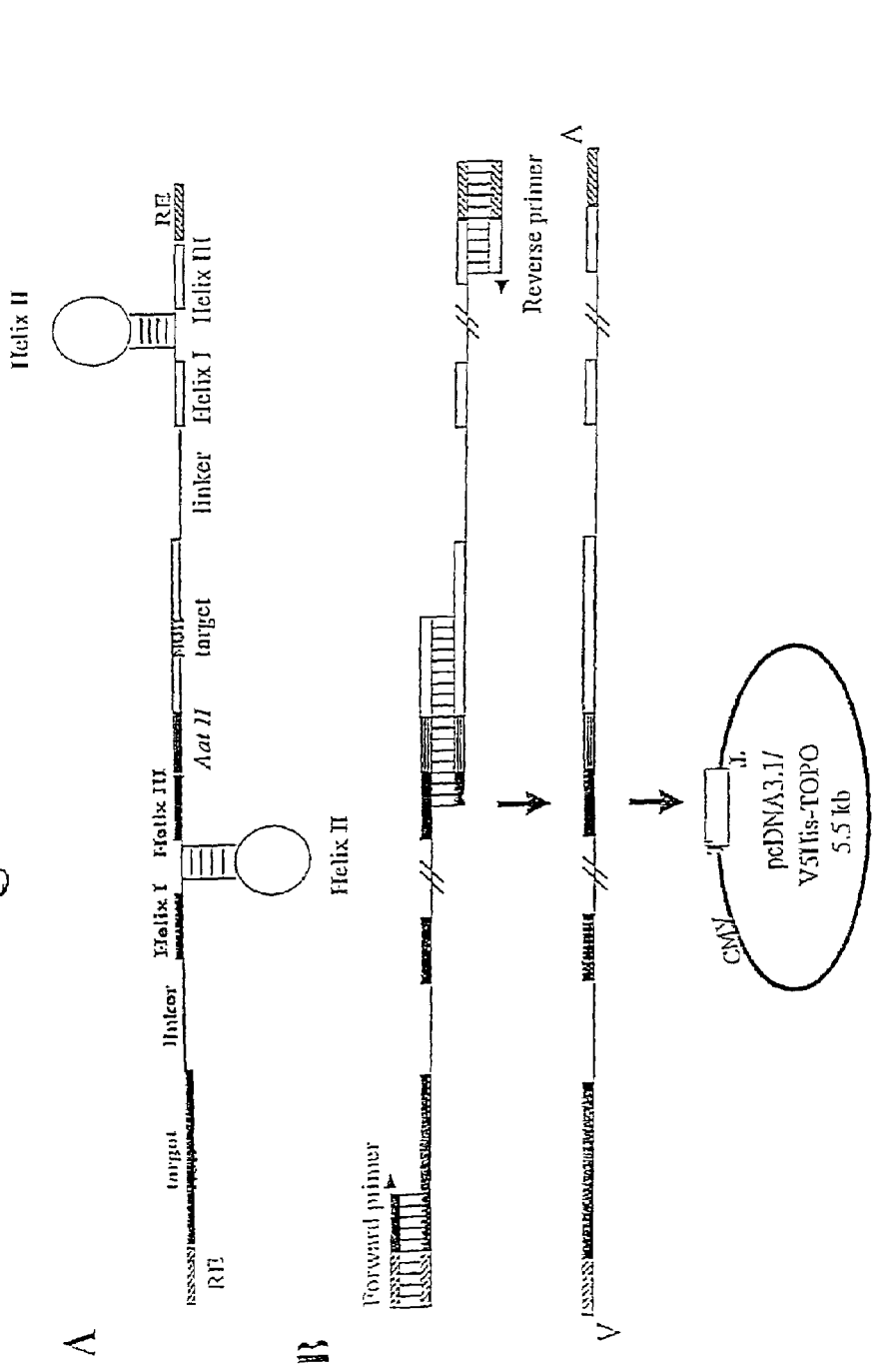
FIGS. 7A–7B: 7A and 7B schematically depict the construction of αhFR multimeric ribozyme by overlap extension PCR.
Figure 8:
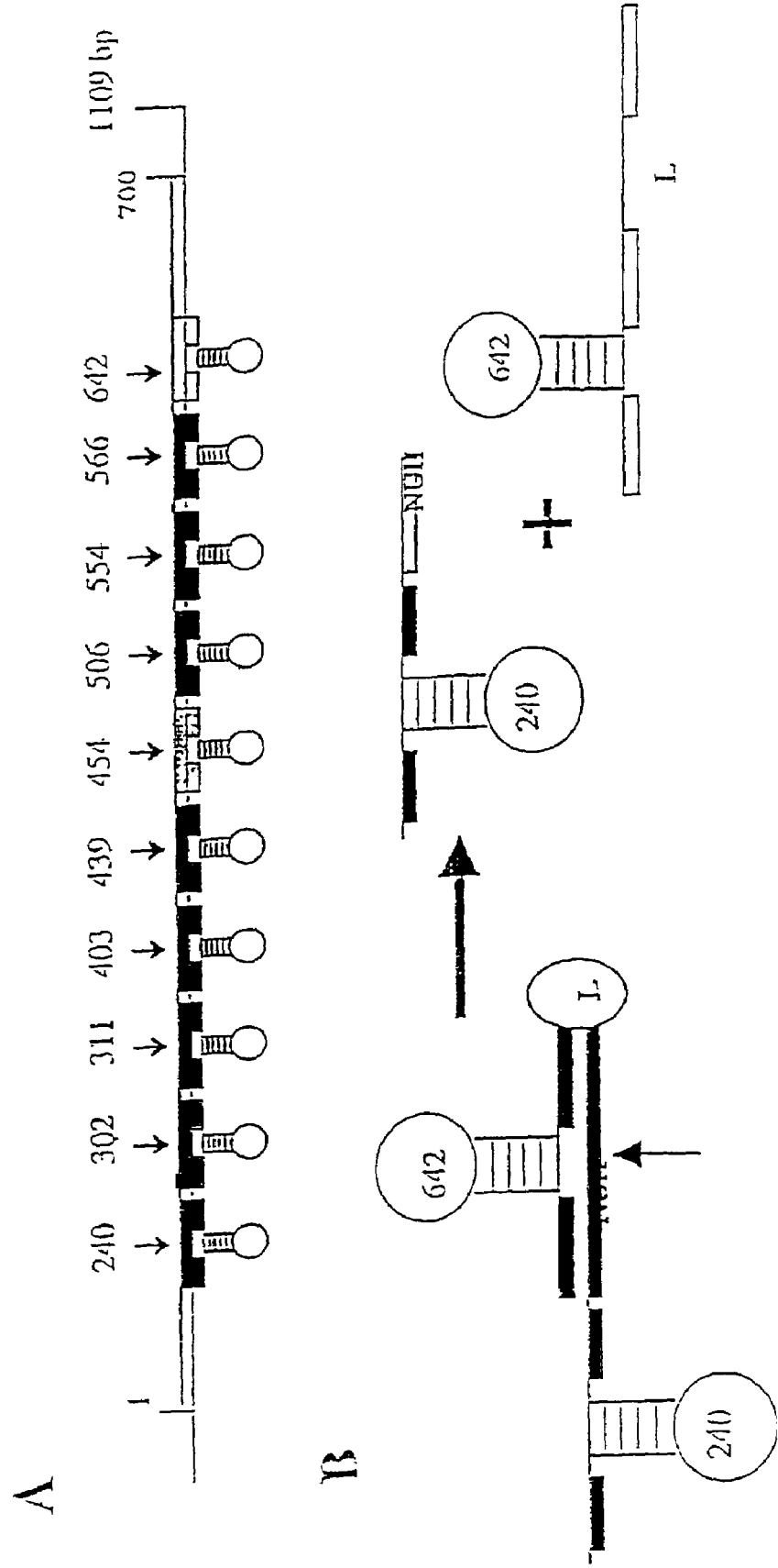
FIGS. 8A–8B: 8A and 8B schematically depict the target locations and self cleavage of αhFR multimeric ribozyme.

Similarly, there are many varieties of ribozymes and their structural derivatives known in the art which may be used in the present invention to target FRα in cells. The common modifications that enhance stability are 2'-O-Me nucleotides in place of 2' hydroxyls, an inverted dibasic sugar at the 3' end, and three or four phosphothioated linkages at the 5' end. It is known in the art how to make and use such modified ribozymes and their structural derivatives, and many are available commercially. Specific examples of such modified ribozymes and their derivatives include: trans-splicing ribozymes and their use in cell abalation (U.S. Pat. Nos. 6,015,794, 6,071,730), stabilized ribozyme analogs (Hybridon, Inc., U.S. Pat. No. 5,545,729), ribozymes with 2'-O-substituted facilitator oligonucleotide (U.S. Pat. Nos. 6,087, 484, 5,612,469), ribozyme analogs having rigid, non-nucleotidic linkers (Hybridon, Inc., U.S. Pat. No. 5,679, 555), other modified ribozymes and optimized minizymes and miniribozymes (U.S. Pat. Nos. 5,672,695, 5,994,124, 6,004,806), and many more known in the art and/or available commercially The ribozymes of the present invention may be single ribozymes containing FRα antisense sequences or maybe comprised of two or more such ribozymes as depicted in FIGS. 7–8, multimeric ribozymes. It is preferred that when multimeric ribozymes are used, the cells and/or the patient be given magnesium and/or calcium supplements to compensate for the mineral depletion, particularly magnesium depletion, from the cells. However, when appropriate other ribozyme systems may be used that are functional under low MG conditions. Mg supplements can be administered alone or together with calcium or other co-factors, either orally or parenterally, e.g. intravenous. The dose can range from milligram amounts up to about 8000 grams per day for severe Mg deficiency. The antisense oligonucleotides of the present invention are useful in therapy of any condition wherein the cells express FRα at higher levels than the normal cells of the same tissue. An example of such condition is ovarian cancer, wherein the neoplastic cells generate high levels of FRα. It is suspected that under physiological conditions wherein the concentrations of reduced folates are low, cells with high numbers of folate receptor alpha are capable of uptake of folic acid, and therefore, proliferate rapidly, forming tumors. Hence, in a similar fashion, in any other tumor system wherein the malignant cells express FRα at high levels, compared to the normal cells of the same tissue, αhFR antisense therapy can be used, effectively. Such other possible malignancies are, but not limited to, the cancer of the cervix, uterus, and brain The antisense oligonucleotides and the pharmaceutical compositions of the present invention may be administered in any fashion that achieve their intended purpose. For example, administration may be by oral or parenteral routes, such as subcutaneous, intravenous, intramuscular, intraperitoneal, or transdermal routes. The dosage administered will be dependent upon the age, health, and weight of the recipient, kind of concurrent treatment, if any, frequency of treatment, and the nature of the effect dsired. The antisense oligonucleotides of the present invention are intended to be used alone or in combination with other therapies, for example, in conjunction with chemotherapy, radiation, surgery, and/or administration of any of the variety of anti-cancer agents Compositions within the scope of this invention include all compositions wherein the antisense oligonucleotide is contained in an amount which is effective to achieve inhibition of proliferation and/or stimulation of differentiation of the subject malignant cells. While individual needs vary, determination of optimal ranges of effective amounts of each component is within the skill in the art. Typically, the antisense oligonucleotides may be administered to mammals, e.g., humans, at a dose of 0.005 to 1 mg/kg/day, or an equivalent amount of the pharmaceutically acceptable salt thereof, per day of the body weight of the mammal being treated.

In addition to administering the antisense oligo as a raw chemical in solution, it may be administered as part of a pharmaceutical preparation containing suitable pharmaceutically acceptable carriers comprising excipients and auxiliaries which facilitate processing of the antisense oligonucleotide into preparations which can be used pharmaceutically.

Suitable formulations for parenteral administration include aqueous solutions of the antisense oligonucleotides in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl cleats or triglycerides. Aqueous injection suspensions may contain substances which increase the viscosity of the suspension, including, for example, sodium carboxymethyl cellulose, sorbitol, and/or dextran. Optionally, the suspension may also contain stabilizers.

The antisense oligonucleotides of the present invention may be prepared according to any of the methods known in the art. Preferably, the antisense oligonucleotides are prepared by solid phase synthesis. See, for example, Goodchild, J., *Bioconjuate Chem.* 1:165–167 (1990), for a review of some chemical synthsis methods well known in the art. Alternatively, the antisense oligonucleotides can be obtained from a number of companies which specialize in the custom synthesis of oligonucleotides Having now generally described this invention, the same will be understood by reference to examples which are provided herein for purposes of illustration only and are not intended to be limiting unless otherwise specified. The entire text of all applications, patents and publications, if any, cited above and below are hereby incorporated by reference.

EXAMPLES

Antisense DNA oligonucleotides and ribozymes were utilized to reduce the expression of αhFR in high expressing (KB) and low expressing (HeLa) αhFR cell lines cultured in low folate media. Antisense oligonucleotide-treated cells exhibited decreased cell proliferation as well as significant inhibition (50–60%) of newly synthesized αhFR protein compared to untreated KB cells. These results indicate that the presence of folate receptors are essential for cell growth and survival in tissue culture under folate restricted conditions. Additionally, ribozymes targeted to the αhFR open reading frame were targeted into cells via the folate receptor using folic acid-polylysine conjugates. The results indicate efficient ribozyme cellular uptake and appropriate substrate cleavage in vitro. Furthermore, cell lines stably transfected with a αhFR cDNA expression vector (pRc/KB2) oriented in the antisense direction failed to form colonies under G418 selection. In contrast, cell lines stabely transfected with αhFR cDNA in the sense orientation survived and formed numerous colonies (>20) under G418 selection (Table III). It appears that expression of antisense αhFR mRNA in cell lines stabely transfected with antisense pRc/KB2 resulted in a knock-out of αhFR function and folate-starved cell death.

Example 1

Reduction of Newly Synthesized αhFR Protein Levels by αhFR Antisense Oligonucleotides Expression of αhFR is known to be elevated in cancer. In particular, increased αhFR expression is found in 90% of human epithelial ovarian malignancies and is associated with a poor disease prognosis. It is possible that over expression of αhFR confers a growth survival advantage in ovarian cancer cells, since folates are involved in numerous cellular processes, including DNA and RNA synthesis. Knocking out receptor function in αhFR-positive cells may therefore prove to be of clinical value in combating ovarian malignancies. Eight different antisense 21 mer oligonucleotides were designed to target the αhFR open reading frame (FIG. 2A) in an attempt to knock out αhFR expression in folate-deficient KB cells, which express significantly high levels of αhFR. FIG. 2B shows that KB cells incubated with 50 µM of AS-1, AS-2 or AS-6 reduced the levels of newly synthesized a αhFR by (up to approximately 60%) compared to KB cells treated with the sense oligonucleotide controls (FIG. 2C). In contrast, Northern analysis of αhFR mRNA remained unaffected by AS-2 or AS-6 treatment (FIG. 2D). This observation suggest that the mechanism by which antisense oligonucleotides reduce αhFR protein levels does not involve destruction of steady state αhFR mRNA by RNase H, a ribonuclease that specifically hydrolyzes DNA/RNA duplexes.

Example 2

Decreased Viability of Cells Treated with a αhFR Antisense Oligonucleotides

Figure 3:
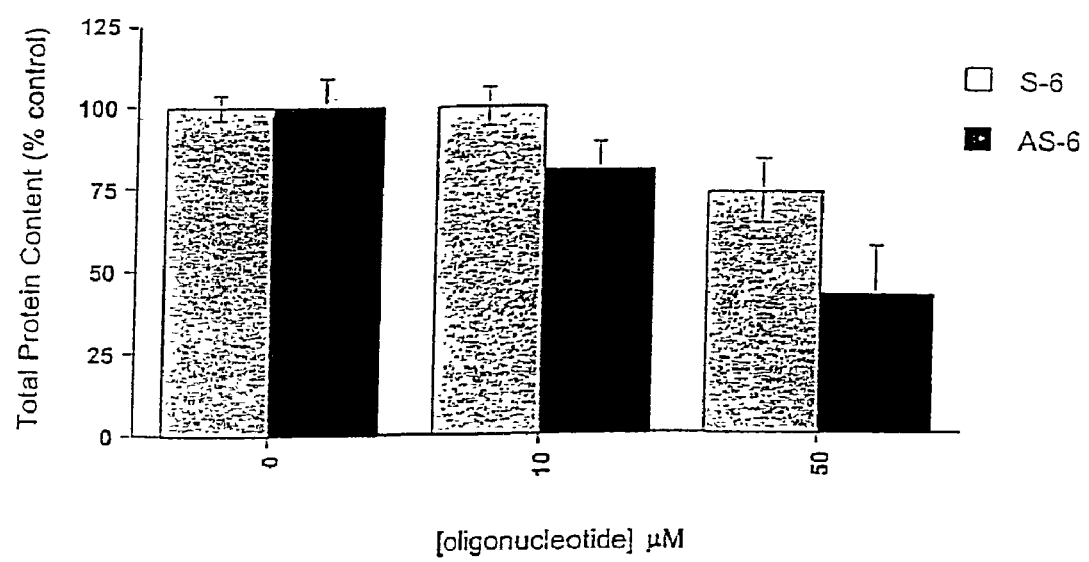
FIG. 3.

The effect of AS-6 on the viability of cultured KB cells was evaluated (FIG. 3). In a reproducible manner, KB cells incubated with 10 or 50 µM AS-6 showed a 20 and 60% decrease, respectively, in overall protein content, compared to the S-6 control. The decrease in cell viability upon AS-6 treatment correlates well with the decrease in newly synthesized αhFR expression, as determined in FIG. 2B. These observations suggest a requirement of αhFR expression for survival of KB cells.

Example 3

αhFR-targeted Ribozymes Efficiently Cleave αhFR mRNA Sequences

Ribozymes are RNAs which are capable of catalyzing RNA cleavage reactions. The hammerhead ribozymes has been extensively studied and involves three putative helical systems: a highly conserved structure that is implicated in catalysis and two flanking regions that can be designed to target the cleavage of the mRNA of interest. Although ribozymes share the potential applications with antisense oligonucleotides, they have the added advantage of catalytic activity that theoretically can allow a single molecule to destroy one or more target RNA. As an alternative approach for knocking out αhFR function, two ribozymes were designed targeted to the 5' region of the αhFR open reading frame (FIG. 4A). FIG. 4B demonstrates efficient cleavage of in vitro synthesized αhFR mRNA sequences by in vitro synthesized αhFR-targeted ribozymes. The correct size cleavage products for Rz 43/65 WT (236 and 846 bp) and Rz 187/210 WT (408 and 701 bp) could be detected after cleavage reactions were gel fractionated and visualized by autoradiography. In contrast, the mutant ribozymes, where *G in the catalytic structure is changed to A, as indicated in FIG. 4A, failed to produce any detectable cleaved product. The data demonstrate functional and efficient cleavage of αhFR mRNA by αhFR-targeted ribozymes.

Example 4

Efficient Transfection and Localization of Oligonucleotides in KB Cells

To test the effect of ribozymes on cell viability we transfected ribozymes into KB cells using cytofectin, a lipid-based transfection vehicle. Cytofectin has been reported to efficiently transfect DNA oligonucleotides in many cell types in the presence or absence of serum in the media. Serum-free conditions are essential for ribozyme transfections since serum is a known source of ribonuclease activity. The transfection efficiency and cellular location of cytofectin-transfected oligonucleotides were determined by transfecting a FITC-labeled DNA oligonucleotide into KB cells. FIG. 5 indicates efficient FITC-labeled oligonucleotide transfection since DAPI stained nuclei in FIG. 5A (blue) and FITC-labeled oligonucleotides in FIG. 5B (green) colocalize well in FIG. 5C.

Example 5

Effect of αhFR-target Ribozymes or Cell Survival

The viability of KB cells transfected with wild type or control mutant and sense ribozymes was assessed by colormetric assay. It was determined that Rz 187/210 WT significantly decreased cell survival by approximately 60% compared to the control mutant and sense ribozymes, Rz 187/210 MUT and Rz 187/210 SEN. (FIG. 6A). Furthermore the data suggest that a knockout of αhFR function by Rz 187/210 WT would involve destruction of αhFR mRNA by cleavage, rather than inhibition of protein synthesis by antisense effect, since the Rz187/210 MUT had little, if any effect on cell survival. Although the ribozymes were expected to be more potent than antisense oligonucleotides with regards to cell survival, the decrease in survival of ribozyme-treated KB cells was similar to what was observed for antisense-treated KB cells in FIG. 3. Also, ribozyme-treated KB cells failed to exhibit a dose-dependent effect, since maximum viability was observed at the lowest ribozyme concentration (5 nM). As shown in FIG. 6B, ribozyme decay was rapid. Approximately 75% of the initial transfected ribozyme amounts disappeared after 1 hour. The quick half-life of ribozyme integrity may explain the unexpected lowered effect of αhFR ribozymes versus antisense oligonucleotides on KB cell survival.

Example 6

The invention can be carried out using multimeric ribozymes. An example of such ribozymes, and the method of making and using them is described below.

Construction of αhFR multimer ribozyme by overlap extension PCR. As shown in FIG. 7A, αhFR ribozymes of the multimeric construct are connected to a cis-positioned target sequence via linker sequences. The complete unit is attached to a second αhFR ribozyme unit by the Aat II restriction enzyme site. The 2-mer ribozyme construct is flanked by unique restriction enzyme sites. FIG. 7B shows how the 2-mer ribozyme is generated by PCR using the overlap extension method in which the overlapping portions of the (+) and (−) DNA templates are extended at 48 degree centigrade in the first round of PCR. The resulting DNA duplex is amplified by forward and reverse end primers at 60 degrees centigrade for 25 cycles. The final product is gel purified and sub-cloned using the TA V5His-TOPO cloning system (Invitrogen, Carlsbad, Calif.). The 2-mer ribozyme units are subsequently connected in tandem via appropriate restriction enzyme sites and then sub-cloned into a pcDNA3.1 eukaryotic expression vector (Invitrogen, Carlsbad, Calif.).

Target location and self cleavage of αhFR multimeric ribozyme. The αhFR ribozymes of a multimeric ribozyme construct, such as the one described above, are targeted to various regions of the αhFR open reading frame. As shown in FIG. 8A, the ribozymes are freed by cleaving cis-positioned target sequences. Freed ribozymes can subsequently cleave in- trans αhFR mRNA transcripts (FIG. 8B).

Example 7

Animal Studies

To examine whether FRα antisense oligos can specifically decrease the amount of FRα expression in tumors, the following experiment is carried out. Athymic mice with subcutaneous tumors expressing high levels of FRα expression are injected with FRα antisense oligos, at various intervals. Appropriate controls, for example, control animals injected with saline or the sense oligo, are set up. The animals are killed, and the tumors are analyzed for the amount they contain of FRα protein. Additionally, the tumor size is measured as described below. It is expected that the tumors injected with FRα antisense oligos will contain decreased amounts of the FRα protein, and that the tumors cease to grow and/or reduce in size.

Example 8

The Impact of αhFR Antisense Oligonucleotide on Survival of Cultured Human Breast Cancer Cells To determine the effect of αhFR antisense oligonucleotide, on the survival of cultured breast cancer cells, we transfected AS6 oligonucleotide and S6 oligonucleotide at various concentrations via the Tf-liposome-mediated gene delivery system. As shown in FIG. 10A, increased amounts of transfected AS6 oligonucleotide correlated with decreased cell survival. The $IC_{50}$ values for the treated breast cancer cell lines are the following: $IC_{50}$=633 nM, T47D, $IC_{50}$=600 nM, MDA-MB-231, and $IC_{50}$=416 nM, MDA-MB-435. In contrast to these data, cell lines treated with S6 oligonucleotide had significantly less effect on the survival of model breast cancer cell lines (FIG. 10B).

Example 9

Figure 11:
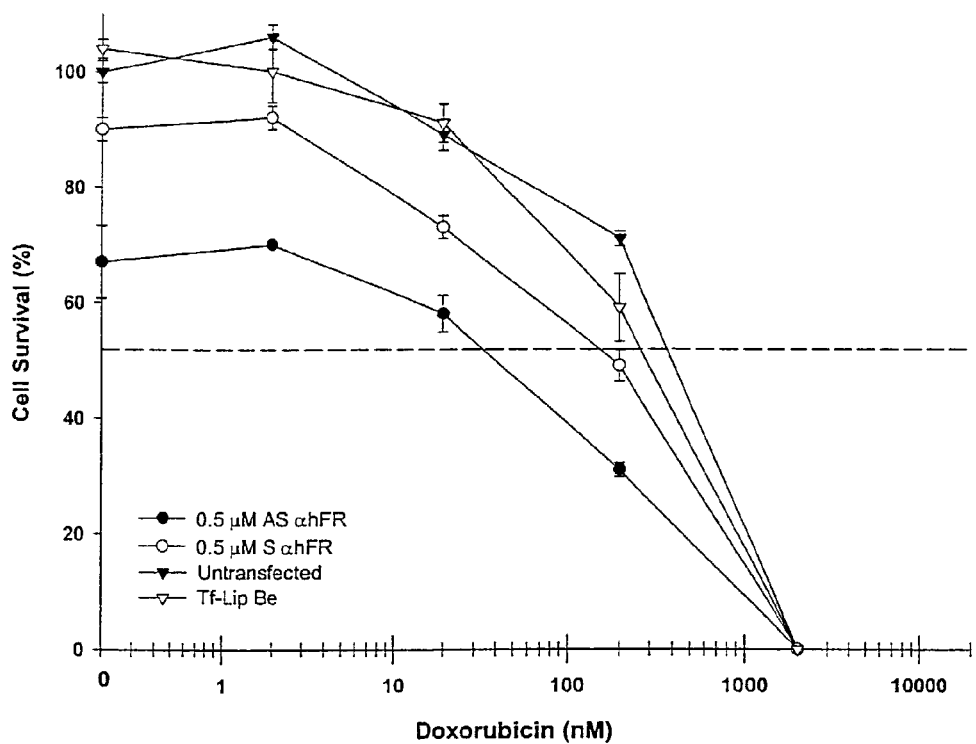
FIG. 11.

Sensitization of MDA-AB435 Breast Cancer Cells to Doxorubicin After Treatment with αhFR Antisense Oligonucleotide To determine whether or not αhFR antisense oligonucleotide sensitizes breast cancer cells to chemotherapy, the following experiment was carried out. 500 nM of AS6 oligonucleotide or S6 oligonucleotide was transfected into MDA-MB-435 cells and treated with varying concentrations of doxorubicin, twenty-four hours after transfection. Cell survival was determined after 72 hrs by XTT assay and the degree of sensitization was calculating by determining the ratio of $IC_{50}$ values of the combined treatment relative to that of the S6 oligonucleotide and untreated controls. In FIG. 11, chemosensitization of MDA-MD-435 cells by AS6 oligonucleotide was about 5 fold ($IC_{50}$ S6/$IC_{50}$ AS6=5) relative to the sense control and about 10 fold ($IC_{50}$ UT/$IC_{50}$ AS6=10) relative to the untreated control.

Example 10

The following are the experimental procedures used to run the experiments described herein. These are only examples of materials and methods useful in the present invention; other materials and methods known to the art may be used interchangeably.

EXPERIMENTAL PROCEDURES

Plasmid Construction. The sense and antisense-oriented αhFR DNAs were subcloned into the eukaryotic expression vector pRc/CMV (Invitrogen, San Diego, Calif.) as outlined in FIG. 1. Briefly, αhFR cDNA was excised from pC32 by EcoRI digestion. The insert was gel-purified and blunt-ended using the Klenow large fragment (Promega, Madison, Wis.). The pRc/CMV vector was prepared by Hind III digestion followed by Klenow fill-in and CIAP reactions (Promega, Madison, Wis.). The vector was blunt-end ligated with the αhFR cDNA insert to generate pRc/CMV αhFR-S and pRc/CMV αhFR-AS. Orientation of the resulting constructs was verified by restriction enzyme and sequencing analyses.

The ribozyme constructs were generated as outlined in FIG. 1. DNA oligonucleotides (See Table II, Ampligene Biotechnologies, Rockville, Md.) encoding αhFR wild type ribozymes (rz43/65 WT and rz187/210 WT), and mutant (rz43/65 MUT and rz187/210 MUT) or sense (rz43/65 S and rz187/210 S) ribozymes were directionally inserted into pGEM4Z- (Promega, Madison, Wis.) via AccI and Hind III restriction enzymes sites and were used for in vitro cleavage reactions. The pGEM-containing wild type/mutant or sense ribozyme constructs (pGEMRz) were subsequently digested with EcoRI and Hind III restriction enzymes. The cleaved insert was gel-purified and then directionally subcloned into EcoRI/Hind III linearized pCDNA 3.1+ (Invitrogen, San Diego, Calif.) to generate eukaryotic wild type/mutant or sense ribozyme expression vectors (pcDNARz) for in vivo studies.

Ribozyme in vitro Cleavage Reactions. Ribozymes were in vitro synthesized from Xba I-digested pGEMRz constructs using the T7 megascript kit (Ambion). [$^{32}$P] labeled αhFR mRNA was generated from Hind II-linearized pC32 using the riboprobe kit (Promega, Madison, Wis.). In vitro cleavge reactions included 1:1 molar ratio of ribozyme:$^{32}$P-labeled αhFR mRNA (~50,000 CPMs/reaction) and 1 µl of 10× cleave buffer (500 mM Tris-HCl, pH 7.5, 10 mM EDTA) to a final volume of 9 µl. The mixture was heated to 95° C. for 5 min and then slowly cooled to RT. Cleavage was initiated by the addition of 1 µl of 200 mM $MgCl_2$. The reaction was incubated for 2 hours at 37° C. and terminated by adding 2 µl of stop solution (95% formamide, 20 mM EDTA, 2% bromophenol blue). The αhFR cleavage products were fractionated by electrophoresis on a 5% sequencing gel for 3 hours and visualized by phosphoimager.

Cell Culture. Wild type human nasopharyngeal epidermoid carcinoma (KB) were obtained from American Type Culture Collection (Rockville, Md.). KB cells were maintained in minimal essential media (DMEM) without folic acid containing L-glutamine, Earl's Salts, and 10% fetal calf serum (Biofluid Inc., Rockville, Md.) at 37° C. at 5% $CO_2$. The final folic acid concentration was approximately 1–10 nM.

DNA oligonucleotides Synthesis, Modification and Fluorescent Labeling. Unmodified DNA oligonucleotides (Table I) were synthesized using an automatic synthesizer (Applied Biosystems). Purity of 21 bp oligonucleotides was assessed by measurement of 260/280 nm absorbance ratios and by electrophoresis analysis on a 10% polyacrylamide gel. Phosphorthioester-modified and FITC-labeled DNA oligonucleotides were generated by Ampligene Biotechnologies (Rockville, Md.).

Northern Analysis. KB cells were maintained over night in growth media containing sense or antisense unmodified DNA oligonucleotides at the indicated concentrations. Total RNA was isolated (Promega, Madison, Wis.) and samples containing 20 µg of total cellular RNA were resolved on a 1% agarose/0.66M formaldehyde/0.023 3-(N-morpholino) propansulfonic acid gel. The RNA's were transferred to a nitrocellulose membrane (Schleicher and Schuell, Portran, Keene, N.H.) and then hybridized to a random $^{32}$P-labeled αhFR cDNA probe as described previously.

Immunoprecipitation. Newly synthesized proteins were radiolabeled by incubating $10^6$ KB cells/35 mm dish in 1 ml of growth media containing 50 µci $^{35}$S-methionine in the presence of sense or antisense ahFR unmodified DNA oligonucleotides at indicated concentrations for 16 hrs. Detection of αhFR was performed exactly as described previously using polyclonal rabbit anti-αhFR antiserum. Proteins were fractionated by SDS PAGE and quantitated by phosporimager analysis.

Cell Viability Experiments. Stable transfectants of pRc/CMV αhFR-S or pRc/CMV ahFR-AS constructs were achieved by the calcium phosphate method using the Stratagene Eukaryotic Transfection kit (La Jolla, Calif.) and selected in 500 µg/ml G418. Phosphorothioated-modified αhFR sense (S-6) and antisense (AS-6) DNA oligonucleotides were transfected into $6\times10^4$ KB cells by incubating oligonucleotides in 1 ml of serum-free media for 6 hrs. Transfections were terminated by the addition of 1 ml of serum-containing low-folate media. Total protein content was assessed 36 hours later by Bradford assay (Biorad, Hercules, Calif.).

In vitro synthesized wild type, mutant or sense-oriented ribozymes were transfected into $6\times10^4$ KB cells with cytofectin (Glen Research, Rockville, Md.), according to manufacturers instruction. Transfections were terminated by replacing media with 1 ml of serum-containing low-folate media. Cell viability was quantitated after 36 hours by the Cell Counting Kit-8 (Dojindo, Gaithersburg, Md.). For ribozyme decay analysis, in vitro synthesized ribozymes were radiolabeled with [α-$^{32}$P]-rCTP and rGTP using the riboprobe kit (Promega, Madison, Wis.). Radiolabeld ribozymes were transfected by the cytofectin method as described above. Total RNA was extracted at the indicated time points using the RNeasy mini kit (Quiagen, Valencia, Calif.), fractionated on a 6% sequencing gel and visualized by autoradiography. Amounts of intact internalized $^{32}$P-labeled ribozyme were determined using the NIH image software.

Fluorercence Oligonucleotides Uptake. KB and HeLa cells were transfected with phosophorthioester-modified and FITC-labeled sense and antisense DNA oligonucleotides as described above. After 16 hrs, transfected cells were collected by centrifugation at 1000 RPM for 5 min and resuspended in 500 µl 3.7% formaldehyde in PBS for 10 min at RT. Cells were collected again by centrifugation and the fixative was replaced by 500 ml of PBS. This step was repeated twice. The final sample was resuspended in 50 µl PBS and was mounted on glass slides by cytospin at 900 RPMs for 5 min. Cells were DAPI- stained by submerging the glass slide into PBS containing 400 ng/ml of DAPI for 10 min at RT in the dark. Glass slides were subsequently washed twice with PBS and air-dried before mounting coverslips with SlowFade (Molecular Probes). Transfected cells were imaged using Zeiss Axiophot microscope interfaced with a CCD camera (Optronics Engineering, Goleta, Calif.).

Animal Studies. KB cells grown in folate-deficient media ($2\times10^6$ cells in 0.1 ml) are inoculated subcutaneously in the back of Bulb C athymic mice. After one week, when tumor size has reached 80–100 mg, tumors are injected with 1 mg/100 µl αhFR sense (S-6) or antisense (AS-6) phosphorothioated-modified DNA oligonucleotides. Tumor regression is evaluated at the indicated time points by calculating tumor volume (formula: $4/3 pr^3$ where r=(length+width)/4) and weight. The excised tumors are later utilized to determine αhFR levels by western analysis as previously described.

TABLE 1

| Primer | Sequence | Target Site in αhFR Open Reading Frame | |
|---|---|---|---|
| Antisense 1 | TGT TGT CAT CCG CTG AGC CAT | 21–1 | (SEQ ID NO. 2) |
| Sense 1 | ATG GCT CAG CGG ATG ACA ACA | 1–21 | |
| Antisense 2 | AGG AGG TCA GCT GAG CAG CCA | 780–760 | (SEQ ID NO. 3) |
| Sense 2 | TGG CTG CTC AGC TGA CCT CCT | 760–780 | |
| Antisense 3 | CTT GTG GTG CTT GGC GTT CAT | 132–112 | |
| Sense 3 | ATG AAC GCC AAG CAC CAC AAG | 112–132 | |
| Antisense 4 | GTA GGA AAC ATC CTT ATG GGC | 240–220 | |
| Sense 4 | GCC CAT AAG GAT GTT TCC TAC | 220–240 | |
| Antisense 5 | GAT CCA GGG CCC CAA GTT GGG | 351–331 | |
| Sense 5 | CCC AAC TTG GGG CCC TGG ATC | 331–351 | |
| Antisense 6 | GCT CTT GCA GGT GTA GGA GGT | 462–442 | (SEQ ID NO. 4) |
| Sense 6 | ACC TCC TAC ACC TGC AAG AGC | 442–462 | |
| Antisense 7 | TTC ATT GCA CAG AAC AGT GGG | 573–553 | |
| Sense 7 | CCC ACT GTT CTG TGC AAT GAA | 553–573 | |
| Antisense 8 | CGC CAC CTC CTC ATT GGG GTT | 678–658 | |
| Sense 8 | AAA CCC AAT GAG GAG GTG GGG | 658–678 | |

TABLE II

| Ribozyme | DNA Oligonucleotide Sequence |
|---|---|
| 43/65 WT | 5' CCC GTC GAC GTG GGT GGC TGT TTC GTC CTC ACG GAC TCA TCA GGT AGG GGA GGA AGC TTC CC 3' |
| | 3' GGG CAG CTG CAC CCA CCG ACA AAG CAG GAG TGC CTG AGT AGT CCA TCC CCT CCT TCG AAG GG 5' |
| 43/65 MUT | 5' CCC GTC GAC GTG GGT GGC TGT TTC GTC CTG ACG GAT TCA TCA GGT AGG GGA GGA AGC TTC CC 3' |
| | 3' GGG CAC CTC CAC CCA CCG ACA AAG CAC GAC TGC CTA AGT AGT CCA TCC CCT CCT TCG AAG GG 5' |
| 43/65 SEN | 5' CCC GTC GAC CAC CCA CCG AGT TTC GTC CTC ACG GAC TCA TCA GCA TCC CCT CCA AGC TTC CC 3' |
| | 3' GGG CAG CTG GTG GGT GGC TCA AAG CAG GAG TGC CTG AGT AGT CGT AGG GGA GGT TCG AAG GG 5' |
| 187/210 WT | 5' CCC GTC GAC AAT GCC TGC TGT TTC GTC CTC ACG GAC TCA TCA GCT ACC AAC ACA AGC TTC CC 3' |
| | 3' GGG CAG CTG TTA CGG ACG ACA AAG CAG GAG TGC CTG AGT AGT CGA TGG TTG TGT TCG AAG GG 5' |
| 187/210 MUT | 5' CCC GTC GAC AAT GCC TGC TGT TTC GTC CTC ACG GAT TCA TCA GCT ACC AAC ACA AGC TTC CC 3' |
| | 3' GGG CAG CTG TTA CGG ACG ACA AAG CAG GAG TGC CTA AGT AGT CGA TGG TTG TGT TCG AAG GG 5' |
| 187/210 SEN | 5' CCC GTC GAC TTA CGG ACG AGT TTC GTC CTC ACG GAC TCA TCA GGA TGG TTG TGA AGC TTC CC 3' |
| | 3' GGG CAG CTG AAT GCC TGC TCA AAG CAG GAG TGC CTC AGT AGT CCT ACC AAC ACT TCG AAG CC 5' |

TABLE III

Cell lines were stably transfected with a pRc/CMV vector encoding αhFR in the sense or antisansa orientation. Stable transfectants were selected for colony formation in 500 μg/mL G418

| Cells | Construct | Colonies |
|---|---|---|
| CHO | Sensa | >20 |
|  | Antisansa | 0 |
| MCF-7 | Sensa | >20 |
|  | Antisansa | 0 |
| KB | Sensa | >0 |
|  | Antisansa | 0 |
| L(tk-) | Sensa | >0 |
|  | Antisansa | 0 |

What is claimed is:

1. An antisense oligonucleotide complementary to a region of the open reading frame of ∀αhFR (SEQ ID NO:1) as shown in FIG. 9, wherein said antisense oligonucleotide is AS6 (SEQ ID NO:4).

2. An oligonucleotide which is a structural derivative of the oligonucleotides claimed in claim 1.

3. The oligonucleotide of claim 2, wherein said oligonucleotide contains internucleotide linkages that are phosphodiesters.

4. The oligonucleotide of claim 2, wherein said oligonucleotide contains internucleotide linkages that are phosphorothioate phosphodiesters.

5. A pharmaceutical composition comprising the antisense oligonucleotide of claim 1 and a pharmaceutically acceptable carrier.

6. A ribozyme containing the antisense oligonucleotide of claim 1.

7. The ribozyme of claim 6, wherein said ribozyme is a hammerhead ribozyme.

8. A multinumeric ribozyme comprising two or more ribozymes as claimed in claim 6.

9. A pharmaceutical composition comprising the ribozyme of any one of claims 6–8 and a pharmaceutically acceptable carrier.

10. The pharmaceutical composition as claimed in claim 8, further comprising magnesium.

11. A vector containing the antisense oligonucleotide of claim 1.

* * * * *

SEQUENCE LISTING

<160> NUMBER OF SEQ ID NOS: 4

<210> SEQ ID NO 1
<211> LENGTH: 1127
<212> TYPE: DNA
<213> ORGANISM: Homo sapiens

<400> SEQUENCE: 1

```
ctggaggcct ggctggtgct cacatacaat aattaactgc tgagtggcct tcgcccaatc      60
ccagcctcca ctcctgggct ccattcccac tccctgcctg tctcctaggc cactaaacca     120
cagctgtccc ctggaataag gcaaggggga gtgtagagca gagcagaagc ctgagccaga     180
cggagagcca cctcctctcc cagggacaga catggctcag cggatgacaa cacagctgct     240
gctccttcta gtgtgggtgg ctgtagtagg ggaggctcag acaaggattg catgggccag     300
gactgagctt ctcaatgtct gcatgaacgc caagcaccac aaggaaaggc caggccccga     360
ggacaagttg catgagcagt gtcgaccctg gaggaagaat gcctgctgtt ctaccaacac     420
cagccaggaa gcccataagg atgtttccta cctatataga ttcaactgga ccactgtgg      480
agagatggca cctgcctgca acggcatttt catccaggac acctgcctct acgagtgctc     540
ccccaacttg gggccctgga tccagcaggt ggatcagagc tggcgcaaag agcgggtact     600
gaacgtgccc ctgtgcaaag aggactgtga gcaatggtgg gaagattgtc gcacctccta     660
cacctgcaag agcaagtggc acaagggctg gaactggact tcagggtttta acaagtgcgc     720
agtgggacgt gcctgccaac ctttccattt ctacttcccc acaccactg ttctgtgcaa      780
tgaaatctgg actcactcct acaaggtcag caactacagc cgagggagtg gccgctgcat     840
ccagatgtgg ttcgacccag cccagggcaa ccccaatgag gaggtggcga ggttctatgc     900
tgcagccatg agtcggggct gggcctggg cagcctggcc tttcctgctt agcctggccc     960
taatgctgct gtggctgctc agctgacctc cttttacctt ctgatacctg gaaatccctg    1020
ccctgttcag ccccacagct cccaactatt tggttcctgc tccatggtcg ggctctgac     1080
agccactttg aataaaccag acaccgcaca aaaaaaaaaaa aaaaaaa                 1127
```

```
<210> SEQ ID NO 2
<211> LENGTH: 21
<212> TYPE: DNA
<213> ORGANISM: homo sapiens

<400> SEQUENCE: 2
tgttgtcatc cgctgagcca t                                      21

<210> SEQ ID NO 3
<211> LENGTH: 21
<212> TYPE: DNA
<213> ORGANISM: homo sapiens

<400> SEQUENCE: 3
aggaggtcag ctgagcagcc a                                      21

<210> SEQ ID NO 4
<211> LENGTH: 21
<212> TYPE: DNA
<213> ORGANISM: homo sapiens

<400> SEQUENCE: 4
gctcttgcag gtgtaggagg t                                      21
```